United States Patent [19]
Goodship et al.

[11] Patent Number: 5,965,547
[45] Date of Patent: Oct. 12, 1999

[54] USE OF CERTAIN METHANEBISHOSPHONIC ACID DERIVATIVES TO PREVENT PROSTHESIS LOOSENING AND PROSTHESIS MIGRATION

[75] Inventors: Allen E. Goodship, Bristol; John Kenwright, Cutts End Cumnor, both of United Kingdom; Jonathan Green, Arlesheim, Switzerland

[73] Assignee: Novartis Corporation, Summit, N.J.

[21] Appl. No.: 08/732,324

[22] PCT Filed: Apr. 24, 1995

[86] PCT No.: PCT/IB95/00288

§ 371 Date: Oct. 28, 1996

§ 102(e) Date: Oct. 28, 1996

[87] PCT Pub. No.: WO95/30421

PCT Pub. Date: Nov. 16, 1995

[30] Foreign Application Priority Data

May 4, 1994 [GB] United Kingdom .................. 9408775

[51] Int. Cl.$^6$ .................................................. A61K 31/66
[52] U.S. Cl. ............................................ 514/102; 514/108
[58] Field of Search ...................... 514/102, 108

[56] References Cited

U.S. PATENT DOCUMENTS

| | | | |
|---|---|---|---|
| 3,962,432 | 6/1976 | Schmidt-Dunker | 424/204 |
| 4,639,338 | 1/1987 | Stahl et al. | 260/502.5 |
| 4,711,880 | 12/1987 | Stahl et al. | 514/108 |
| 4,939,130 | 7/1990 | Jaeggi et al. | 514/94 |
| 5,403,829 | 4/1995 | Lehjtinen et al. | 514/102 |
| 5,646,134 | 7/1997 | Yates | 514/108 |

FOREIGN PATENT DOCUMENTS

| | | |
|---|---|---|
| 0513760 | 11/1992 | European Pat. Off. . |
| 9421266 | 9/1994 | WIPO . |

OTHER PUBLICATIONS

Journal Bone Miner Res, vol. 8, No. Supp 2 1993 pp. S563–S564.
Clin Orthop Relat Res, vol. 287, 1993 pp. 61–67.
Clin Orthop Relat. Res. vol. 167 1982, pp. 106–112.
ACTA Orthop. Scand. vol. 64(5) 1993 H96–506, Henrik. Mal Chau et al.
Clinical Orthopaedics and Related Research vol. 282, Sep. 1992, pp. 73–80 Michael Winter et al.
Clinical Orthodpaedics and Related Research vol. 285, Dec. 1992 pp. 45–47 B Mike Wroblewski et al.
Journal of Bone & Joint Surgery vol. 72–B, No. 3, May 1990. J.Wilson Mac Donald et al.
Bone & Mineral, vol. 20 (1993) pp. 67–78. Acke Ohlin et al.
Journal of Rheumatology 1994, vol. 21 No. 2, pp. 338–343 Jerome H. Herman et al.
Journal of Nuclear Medicine vol. 34 No. 12. Dec. 1993, B David Pollier et al. pp. 2241–2246.
Journal of Nuclear Medicine, vol. 34, No. 12, Dec. 1993, J. Fogelman et al. pp. 2247–2252.
Clinical Orthopaedics and Related Research, vol. 263, Feb., 1991, pp. 13–29.
The Hip (1987) pp. 59–69, B. J. Thomas et al.
Orthodedic Clinics of North America, vol. 23 No. 2, Apr. 1992, B J Thomas, pp. 347–358.
The Lancet, Jan. 7, 1984. pp. 27–33, John A. Kanis.
The Lancet, Jan. 23, 1988, pp. 143–146. Reid et al.
The Lancet, vol. 342 Dec. 11, 1993. Adamson et al. pp. 1459–1460.
Handbook of Expl. Pharmacology vol. 83, (1988) pp. 441–465. Bers. et al.
Medline Abstract No. 93213656 [Abstract of Medline M. Passer Ann. Itol Med. Int 7 (3 Suppl)137S–153S (Jul.–Sep. 1992] .
Journal of Bone & Joint Surgery vol. 72–B. No. 5, Sep. 1990 pp. 757–760.
B10S is (Acc. No. 83020774) abstract of J. of the Formosan Medical Association 85(6) pp. 554–560 (1986).

*Primary Examiner*—Theodore J. Criares
*Attorney, Agent, or Firm*—Gregory D. Ferraro

[57] ABSTRACT

The invention relates to the use of certain methanebisphosphonic acid derivatives (for the manufacture of a pharmaceutical composition) for the prevention and treatment of prosthesis loosening and prosthesis migration in mammals including man.

5 Claims, No Drawings

USE OF CERTAIN METHANEBISHOSPHONIC ACID DERIVATIVES TO PREVENT PROSTHESIS LOOSENING AND PROSTHESIS MIGRATION

This is a 371 of PCT/IB 95/00288, filed Apr. 25, 1995.

Arthroplasty, especially of the hip joint, is now a common procedure for the treatment of patients with osteoarthritis, rheumatoid arthritis and osteoporotic fracture. Approximately 800 000 hip replacements are performed globally each year. This number is rising steadily, younger patients are being treated and patients are living much longer and they all expect to lead a mobile, independent life. Despite the indisputable success of this technique, often complications arise and may eventually require costly surgical revision (3 or 4 revisions being not uncommon for a single patient).

The most common complications are aseptic prosthesis loosening [see for example H. Malchau et al., Acta Orthop. Scand. 64 (1993) 497–506; R. D. Mulroy Jr. and W. H. Harris, J. Bone Joint Surg. (Br) 72-B (1990) 757–760; M. Winter et al., Clin. Orthop. Rel. Research 282 (1992) 73–80] and migration of the prosthesis through bone without overt loosening [see for example B. B. Wroblewski and P. D. Siney, Clin. Orthop. Rel. Research 285 (1992) 45–47; M. Winter et al., loc. cit.]. These complications result in considerable morbidity, such as pain and reduced mobility. They occur with both cemented and uncemented prostheses, regardless of design, material or coating.

Previous approaches to prevent these complications have concentrated on alterations to the design of the prosthesis and the selection of different materials for its construction [see for example H. Malchau et al., loc. cit.; R. D. Mulroy Jr. and W. H. Harris, loc. cit.; M. Winter et al., loc. cit.; B. B. Wroblewski and P. D. Siney, loc. cit.; J. Wilson-MacDonald et al., J. Bone Joint Surg. (Br) 72-B (1990) 423–430]. Apart from some preliminary research with non-steroidal anti-inflammatory drugs [A. Ohlin and U. H. Lemer, Bone and Mineral 20 (1993) 67–78; J. H. Herman et al., J. Rheumatol. 21 (1994) 338–343], a pharmacological approach to prevent or treat the complications of arthroplasty, especially hip arthroplasty, has not been successful.

Methanebisphosphonic acid derivatives, in particular bisphosphonate compounds (=bisphosphonates), are used clinically to inhibit excessive bone resorption in a variety of diseases such as tumour-induced osteolysis, Paget's disease and osteoporosis [H. Fleisch, Handbook of Expl. Pharmacol. 83 (1988) 441–465]. Radiolabelled bisphosphonates are also used diagnostically to identify sites of high bone turnover [B. D. Collier et al., J. Nucl. Med. 34 (1993) 2241–2246; I. Fogelman et al., J. Nucl. Med. 34 (1993) 2247–2252].

In the orthopaedic field in general, there is a strong prejudice against using bisphosphonates. Firstly, attempts to use the commercially available bisphosphonate etidronate in the prevention of heterotopic ossification - which is another complication after arthroplasty but is very different from prosthesis loosening and prosthesis migration—proved either ineffective, or even detrimental due to a rebound effect [see for example D. E. Garland, Clin. Orthop. Rel. Research 263 (1991) 13–29; B. J. Thomas and H. C. Amstutz, The Hip 1987, 59–69; B. J. Thomas, Orthop. Clin. North America 23 (1992) 347–358].

Furthermore, there is increasing evidence that some bisphosphonates may inhibit bone formation and mineralization. Kanis, for example, teaches in Lancet 1984, 27–33 that bisphosphonates, as inhibitors of bone resorption, may delay the repair of microfractures by reducing the rate of remodelling. As another example, Reid et al. in Lancet 1988, 143–146 found that bisphosphonate treatment, in this particular case done with disodium pamidronate, caused a reduction in bone formation and a very low rate of bone turnover which raised the possibility of impaired microfracture repair. Adamson et al. [Lancet 342 (1993) 1459–1460] reports that pamidronate may inhibit bone mineralization in Paget's disease.

Surprisingly, it has now been found that certain methanebisphosphonic acid derivatives are useful for the cost-effective prevention or treatment of these complications of joint replacement, especially hip replacement, in mammals including man.

This can be demonstrated by appropriate in vitro and in vivo tests. In particular, in vivo experiments show that the bisphosphonates according to the invention are effective in preventing prosthesis loosening in the treated animals, e.g. sheep. This is demonstrated, for example, by the following test methods: 12 adult female sheep, approx. 50 kg body weight, are randomly divided into 2 groups of 6 animals and all undergo a unilateral total hip replacement operation with implantation of a titanium prosthesis. Immediately after surgery one group of animals receives an i.v. infusion of bisphosphonate and the other group receives saline. This treatment may be subsequently repeated, for example at 4 and 8 weeks. At regular monthly intervals the hip and femoral region of each animal is subjected to both standard and quantitative digital radiography to assess changes in bone density around the prosthesis as an early indicator of prosthesis loosening. In addition the animals are walked over a Kistler force plate to measure vertical ground reaction force from both hind limbs to determine limb functionality and, indirectly, pain. At 12 months after the operation, and 2 weeks prior to sacrifice, the animals receive a double injection, 10 days apart, of the fluorescent bone label oxytetracycline to facilitate histomorphometric analysis. At the end of the labelling period the animals are killed and the femurs with the implants are removed for post-mortem analysis. Precision sections, cut and polished from the femurs, are subjected to microradiography to determine bone loss around the implant Similar sections are also analyzed by histomorphometry to assess bone resorption and formation at the tissue level. Finally sections of bone containing the implant are subjected to a mechanical "push-out" test on a materials testing machine to measure the strength of bonding between the metal implant and the surrounding bone.

A comparison of the test animals treated with a bisphosphonate according to the invention with the controls clearly shows that bisphosphonate treatment is beneficial to prevent and treat prosthesis loosening.

The invention therefore relates to the use of a methanebisphosphonic acid derivative selected from 3-amino-1-hydroxypropane-1,1-diphosphonic acid (pamidronic acid), e.g. pamidronate; 3-(N,N-dimethylamino)-1-hydroxypropane-1,1-diphosphonic acid, e.g. dimethyl-APD; 4-amino-1-hydroxybutane-1,1-diphosphonic acid (alendronic acid), e.g. alendronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid; 1-hydroxy-2-(3-pyridyl)ethane-1,1-diphosphonic acid (risedronic acid), e.g. risedronate, including N-methyl pyridinium salts thereof, for example N-methyl pyridinium iodides such as NE-1 0244 or NE-1 0446; 1-(4-chlorophenylthio)methane-1,1-diphosphonic acid (tiludronic acid), e.g. tiludronate; 3-[N-(2-phenylthioethyl)-N-methylamino]-1-hydroxypropane-1,1-diphosphonic acid; 1-hydroxy-3-(pyrrolidin-1-yl)propane-1,1-diphosphonic acid, e.g. EB 1053 (Leo); 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); 1-hydroxy-2-(imidazo[1,2-a]pyridin-3-yl)ethane-1,1-diphosphonic acid, e.g. YM 529; and 1,1-dichloromethane-1,1-diphosphonic acid (clodronic acid), e.g. clodronate; or a pharmaceutically acceptable salt thereof, or any hydrate thereof, (for the manufacture of a pharmaceutical composition) for the prevention and treatment of prosthesis loosening and prosthesis migration in mammals including man.

As already mentioned above, prosthesis loosening and prosthesis migration often occurs as a complication after arthoplasty. Arthroplasty means a partial, e.g. hemi, or total arthroplasty of any joint, especially hip and knee, and in particular hip.

Pharmaceutically acceptable salts are preferably salts with bases, conveniently metal salts derived from groups Ia, Tb, IIa and IIb of the Periodic Table of the Elements, including alkali metal salts, e.g. potassium and especially sodium salts, or alkaline earth metal salts, preferably calcium or magnesium salts, and also ammonium salts with ammonia or organic amines.

Especially preferred pharmaceutically acceptable salts are those where one, two, three or four, in particular one or two, of the acidic hydrogens of the bisphosphonic acid are replaced by a pharmaceutically acceptable cation, in particular sodium, potassium or ammonium, in first instance sodium.

A very preferred group of pharmaceutically acceptable salts is characterized by having one acidic hydrogen and one pharmaceutically acceptable cation, especially sodium, in each of the phosphonic acid groups.

All the methanebisphosphonic acid derivatives mentioned above are well known from the literature. This includes their manufacture (see e.g. EP-A-513 760, pp. 13–48). For example, 3-amino-1-hydroxypropane-1,1-diphosphonic acid is prepared as described e.g. in U.S. Pat. No. 3,962,432 as well as in U.S. Pat. Nos. 4,639,338 and 4,711,880, and 1-hydroxy-2-(imidazol-1-yl)ethane-1,1-diphosphonic acid is prepared as described e.g. in U.S. Pat. No. 4,939,130.

A particular embodiment of the invention is represented by the use of a methane-bisphosphonic acid derivative which is selected from 3-amino-1-hydroxypropane-1,1-diphosphonic acid, 3-(N,N-dimethylamino)-1-hydroxypropane-1,1-diphosphonic acid, 4-amino-1-hydroxybutane-1,1-diphosphonic acid, 6-amino-1-hydroxyhexane-1,1-diphosphonic acid, 3-(N-methyl-N-n-pentylamino)-1-hydroxypropane-1,1-diphosphonic acid, 1-hydroxy-2-(imidazol- 1 -yl)ethane-1,1-diphosphonic acid; 1-hydroxy-2-(3-pyridyl)ethane-1,1-diphosphonic acid, and N-methyl pyridinium salts thereof; 1-(4-chlorophenylthio)methane- 1,1-diphosphonic acid, 3-[N-(2-phenylthioethyl)-N-methylamino]-1-hydroxypropane-1,1-diphosphonic acid; 1-hydroxy-3-(pyrrolidin- 1-yl)propane- 1,1-diphosphonic acid, 1-(N-phenylaminothiocarbonyl)methane-1,1-diphosphonic acid, 5-benzoyl-3,4dihydro-2H-pyrazole-3,3-diphosphonic acid tetraethyl ester, 1-hydroxy-2-(imidazo[1,2-a]pyridin-3-yl)ethane-1,1-diphosphonic acid, a pharmaceutically acceptable salt thereof, and any hydrate thereof.

A preferred embodiment of the invention is represented by the use of a methane-bisphosphonic acid derivative which is selected from 3-amino-1-hydroxypropane-1,1-diphosphonic acid, 3-(N,N-dimethylamino)-1-hydroxypropane-1,1-diphosphonic acid, 4-amino-1-hydroxybutane-1,1-diphosphonic acid, 6-amino-1-hydroxyhexane-1,1-diphosphonic acid, 3-(N-methyl-N-n-pentylamino)- 1-hydroxypropane- 1,1-diphosphonic acid, 1-hydroxy-2-(imidazol-1-yl)ethane-1,1-diphosphonic acid; 1-hydroxy-2-(3-pyridyl)ethane-1,1-diphosphonic acid, 3-[N-(2-phenylthioethyl)-N-methylamino]-1-hydroxypropane- 1,1 -diphosphonic acid; 1-hydroxy-3-(pyrrolidin- 1 -yl)propane- 1,1-diphosphonic acid, 1-hydroxy-2-(imidazo[1,2-a]pyridin-3-yl)ethane-1,1-diphosphonic acid, a pharmaceutically acceptable salt thereof, and any hydrate thereof.

A very preferred embodiment of the invention is represented by the use of a methane-bisphosphonic acid derivative which is selected from pamidronic acid, alendronic acid, 3-(N-methyl-N-n-pentylamino)-1-hydroxypropane-1,1-diphosphonic acid, 1-hydroxy-2-(imidazol-1-yl)ethane-1,1-diphosphonic acid, risedronic acid and tiludronic acid, a pharmaceutically acceptable salt thereof, and any hydrate thereof.

An especially preferred embodiment of the invention is represented by the use of a methanebisphosphonic acid derivative which is selected from 1-hydroxy-2-(imidazol-1-yl)ethane- 1,1 -diphosphonic acid and 3-amino-1-hydroxypropane-1,1-diphosphonic acid, a pharmaceutically acceptable salt thereof, and any hydrate thereof.

Further the invention relates to the use of 1-hydroxy-2-(imidazol-1-yl)ethane-1,1-diphosphonic acid or a pharmaceutically acceptable salt thereof or any hydrate thereof.

Further the invention relates to the use of 3-amino-1-hydroxypropane-1,1-diphosphonic acid or a pharmaceutically acceptable salt thereof or any hydrate thereof.

The pharmaceutically useful methanebisphosphonic acid derivatives may be used in the form of a possible isomer or of a mixture of isomers, typically as optical isomers such as enantiomers or diastereoisomers or geometric isomers, typically cis-trans isomers. The optical isomers are obtained in the form of the pure antipodes and/or as racemates.

The pharmaceutically useful methanebisphosphonic acid derivatives can also be used in the form of their hydrates or include other solvents used for their crystallisation.

The methanebisphosphonic acid derivative is preferably used in the form of a pharmaceutical preparation that contains a therapeutically effective amount of the active ingredient optionally together with or in admixture with inorganic or organic, solid or liquid, pharmaceutically acceptable carriers which are suitable for administration.

The pharmaceutical compositions may be, for example, compositions for enteral, such as oral, rectal, aerosol inhalation or nasal administration, compositions for parenteral, such as intravenous or subcutaneous administration, or compositions for transdermal administration (e.g. passive or iontophoretic). Furthermore, direct local administration at the time of operation comes into consideration. What is meant by the latter type of administration is the coating of the exposed bone surface to which the implant is attached, with a bisphosphonate according to the invention, for example by washing the bone surface with a bisphosphonate solution. What is not meant by this type of administration is the coating of the prosthesis with bisphosphonates.

Preferably, the pharmaceutical compositions are adapted to oral or parenteral (especially intravenous or transdermal) administration before, during or after prosthesis implantation, or to local administration during prosthesis implantation. Intravenous and oral, first and foremost intravenous, administration is considered to be of particular importance.

The particular mode of administration and the dosage will be selected by the attending physician taking into account the particulars of the patient, especially age, weight, life style, activity level, hormonal status (e.g. postmenopausal), bone mineral density and type of prosthesis to be implanted.

The dosage of the active ingredient may depend on various factors, such as effectiveness and duration of action of the active ingredient, mode of administration, warm-blooded species, and/or sex, age, weight and individual condition of the warm-blooded animal.

Normally the dosage is such that a single dose of from 0.002–3.40 mg/kg, especially 0.01–2.40 mg/kg, is administered to a warm-blooded animal weighing approximately 75 kg,. If desired, this dose may also be taken in several, optionally equal, partial doses.

"mg/kg" means mg drug per kg body weight of the mammal—including man—to be treated.

The dose mentioned above—either administered as a single dose (which is preferred) or in several partial doses—may be repeated, for example once daily, once weekly, once every month, once every three months, once every six months or once a year. In other words, the pharmaceutical compositions may be administered in regimens ranging from continuous daily therapy to intermittent cyclical therapy.

Preferably, the methanebisphosphonic acid derivatives are administered in doses which are in the same order of magnitude as those used in the treatment of thee diseases classically treated with methanebisphosphonic acid derivatives, such as Paget's disease, tumour-induced hypercalcaemia or osteoporosis. In other words, preferably the methanebisphosphonic acid derivatives are administered in doses which would likewise be therapeutically effective in the treatment of Paget's disease, tumour-induced hypercalcaemia or osteoporosis, i.e. preferably they are administered in doses which would likewise effectively inhibit bone resorption.

Formulations in single dose unit form contain preferably from about 1% to about 90%, and formulations not in single dose unit form contain preferably from about 0.1% to about 20%, of the active ingredient. Single dose unit forms such as capsules, tablets or dragees contain e.g. from about 1 mg to about 500 mg of the active ingredient.

The invention further relates to the use of a composition for the manufacture of a medicament, e.g. in single dose unit form, for the prevention and treatment of prosthesis loosening and prosthesis migration in mammals including man, wherein the composition contains 0.002–3.40 mg/kg, especially 0.01–2.40 mg/kg, of a methanebisphosphonic acid derivative as defined above per dosage form.

Moreover, the invention relates to the use of a methanebisphosphonic acid derivative as defined above at a dose of 0.002–3.40 mg/kg, especially 0.01–2.40 mg/kg, per dosage form for the manufacture of a medicament for the prevention and treatment of prosthesis loosening and prosthesis migration in mammals including man.

Pharmaceutical preparations for enteral and parenteral administration are, for example, those in dosage unit forms, such as dragees, tablets or capsules and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or dragee cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, crosslinked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Drage cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers.

Suitable formulations for transdermal application include an effective amount of the active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

The following Examples illustrate the invention described hereinbefore. The term "active ingredient" is to be understood as being any one of the methanebisphosphonic acid derivatives mentioned above as being useful according to the present invention.

Example 1: Capsules containing coated pellets of, for example, disodium pamidronate pentahydrate, as active ingredient:

| Core pellet: | |
|---|---|
| active ingredient (ground) | 197.3 mg |
| Microcrystalline cellulose (Avicel ® PH 105) | 52.7 mg |
| | 250.0 mg |
| + Inner coating: | |
| Cellulose HP-M 603 | 10.0 mg |
| Polyethylene glycol | 2.0 mg |
| Talc | 8.0 mg |
| | 270.0 mg |
| + Gastric juice-resistant outer coating: | |
| Eudragit ® 30 D (solid) | 90.0 mg |
| Triethyl citrate | 21.0 mg |
| Antifoam ® AF | 2.0 mg |
| Water | |
| Talc | 7.0 mg |
| | 390.0 mg |

A mixture of disodium pamidronate with Avicel®D PH 105 is moistened with water and kneaded, extruded and formed into spheres. The dried pellets are then successively coated in the fluidized bed with an inner coating, consisting of cellulose HP-M 603, polyethylene glycol (PEG) 8000 and talc, and the aqueous gastric juice-resistant coat, consisting of Eudragit® L 30 D, triethyl citrate and Antifoam® AF. The coated pellets are powdered with talc and filled into capsules (capsule size 0) by means of a commercial capsule filling machine, for example Höfliger and Karg.

Example 2: Monolith adhesive transdermal system, containing as active ingredient, for example, 1-hydroxy-2-(imidazol-1-yl)-ethane-1,1-diphosphonic acid:

| Composition: | |
|---|---|
| polyisobutylene (PIB) 300 (Oppanol B1, BASF) | 5.0 g |
| PIB 35000 (Oppanol B10, BASF) | 3.0 g |
| PIB 1200000 (Oppanol B100, BASF) | 9.0 g |
| hydrogenated hydrocarbon resin (Escorez 5320, Exxon) | 43.0 g |
| 1-dodecylazacycloheptan-2-one (Azone, Nelson Res., Irvine/CA) | 20.0 g |
| active ingredient | 20.0 g |
| Total | 100.0 g |

Preparation:

The above components are together dissolved in 150 g of special boiling point petroleum fraction 100–125 by rolling on a roller gear bed. The solution is applied to a polyester film (Hostaphan, Kalle) by means of a spreading device using a 300 μm doctor blade, giving a coating of about 75 g/m². After drying (15 minutes at 60° C.), a silicone-treated polyester film (thickness 75 μm, Laufenberg) is applied as the peel-off film. The finished systems are punched out in sizes in the wanted form of from 5 to 30 cm² using a punching tool. The complete systems are sealed individually in sachets of aluminised paper.

Example 3: Vial containing 1.0 mg dry, lyophilized 1-hydroxy-2-(imidazol-1-yl)-ethane-1,1-diphosphonic acid (mixed sodium salts thereof). After dilution with 1 ml of water, a solution (concentration 1 mg/ml) for i.v. infusion is obtained.

| Composition: | | |
|---|---|---|
| active ingredient (free diphosphonic acid) | | 1.0 mg |
| mannitol | | 46.0 mg |
| Trisodium citrate × 2 H₂O | ca. | 3.0 mg |
| water | | 1 ml |
| water for injection | | 1 ml. |

In 1 ml of water, the active ingredient is titrated with trisodium citrate×2 H₂O to pH 6.0. Then, the mannitol is added and the solution is lyophilized and the lyophilisate filled into a vial.

Example 4: Ampoule containing disodium pamidronate pentahydrate dissolved in water. The solution (concentration 3 mg/ml) is for i.v. infusion after dilution.

| Composition: | |
|---|---|
| active ingredient (≙ 15.0 mg of anhydrous active ingredient) | 19.73 mg |
| mannitol | 250 mg |
| water for injection | 5 ml. |

Example 5: Tablets each containing 50 mg of 3-[N-(2-phenylthioethyl)-N-methylamino]-1-hydroxypropane-1,1-diphosphonic acid can be prepared as follows:

| Composition (10,000 tablets) | |
|---|---|
| Active ingredient | 500.0 g |
| Lactose | 500.0 g |
| Potato starch | 325.0 g |
| Gelatin | 8.0 g |
| Talc | 60.0 g |
| Magnesium stearate | 10.0 g |
| Silicon dioxide (finely divided) | 20.0 g |
| Ethanol | q.s. |

The active ingredient is mixed with the lactose and 292 g of potato starch, and the mixture is moistened with an ethanolic solution of the gelatin and granulated through a sieve. After the granules have dried, the remainder of the potato starch, the magnesium stearate and the silicon dioxide are admixed and the mixture compressed to give tablets each weighing 145.0 mg, and containing 50.0 mg of active ingredient, which can, if desired, be provided with breaking, grooves to enable the dosage to be more finely adjusted.

We claim:

1. A method of preventing or treating prosthesis loosening and prosthesis migration in mammals, which comprises administering to a mammal in need thereof a therapeutically effective amount of 1 -hydroxy-2-(imidazol-1-yl)ethane-1, 1-diphosphonic acid[; 1-hydroxy-2-(3-pyridyl)ethane-1,1-diphosphonic acid, and N-methyl pyridinium salts thereof; 1-(4-chlorophenylthio)methane-1,1-diphosphonic acid, 3-[N-(2-phenylthioethyl)-N-methylamino]-1- hydroxypropane-1,1-diphosphonic acid; 1-hydroxy-3-(pyrrolidin-1-yl)propane-1,1-diphosphonic acid, 1-(N-phenyl-aminothiocarbonyl)methane-1,1-diphosphonic acid, 5-benzoyl-3,4-dihydro2H-pyrazole-3,3-diphosphonic acid tetraethyl ester, 1-hydroxy-2-(imidazo or a pharmaceutically acceptable salt thereof, or any hydrate thereof.

2. A method according to claim 1, wherein the prosthesis is a hip prosthesis.

3. A method according to claim 1, wherein the 1-hydroxy-2-(imidazol-1-yl)ethane-1,1-diphosphonic acid is administered intravenously.

4. A method according to claim 1, wherein the 1-hydroxy-2-(imidazol-1-yl)ethane-1,1-diphosphonic acid is administered transdermally.

5. A method according to claim 1, wherein the 1-hydroxy-2-(imidazol-1-yl)ethane-1,1-diphosphonic acid is administered orally.

\* \* \* \* \*

UNITED STATES PATENT AND TRADEMARK OFFICE
CERTIFICATE OF CORRECTION

PATENT NO. : 5,965,547
DATED : October 12, 1999
INVENTOR(S) : GOODSHIP ET AL.

It is certified that error appears in the above-identified patent and that said Letters Patent is hereby corrected as shown below:

In claim 1, beginning at line 5, please delete "[; 1-hydroxy-2-(3-pyridyl)ethane-1,1-diphosphonic acid, and N-methyl pyridinium salts thereof; 1-(4-chlorophenylthio)methane-1,1-diphosphonic acid, 3-›N-(2-phenylthioethyl)-N-methylamino!-1-hydroxypropane-1,1-diphosphonic acid; 1-hydroxy-3-(pyrrolidin-1-yl)propane-1,1-diphosphonic acid, 1-(N-phenyl-aminothiocarbonyl)methane-1,1-diphosphonic acid, 5-benzoyl-3,4-dihydro2H-pyrazole-3,3-diphosphonic acid tetraethyl ester, 1-hydroxy-2-(imidazo".

Signed and Sealed this

Twelfth Day of December, 2000

Attest:

Q. TODD DICKINSON

*Attesting Officer*     *Director of Patents and Trademarks*